United States Patent
Di Giovanni et al.

(10) Patent No.: US 6,966,467 B2
(45) Date of Patent: Nov. 22, 2005

(54) VALVE FOR AEROSOL CONTAINER

(75) Inventors: Patrick Di Giovanni, Le Vaudrueil (FR); Cheryl Vanessa Rogerson, Essex (GB)

(73) Assignee: SmithKlineBeecham Corporation, Philadelphia, PA (US)

(*) Notice: Subject to any disclaimer, the term of this patent is extended or adjusted under 35 U.S.C. 154(b) by 0 days.

(21) Appl. No.: 10/347,092

(22) Filed: Jan. 17, 2003

(65) Prior Publication Data

US 2003/0136802 A1 Jul. 24, 2003

Related U.S. Application Data

(63) Continuation of application No. 09/957,916, filed on Sep. 21, 2001, now Pat. No. 6,510,969, which is a continuation of application No. 09/709,084, filed on Nov. 10, 2000, now Pat. No. 6,315,173, which is a continuation of application No. 09/331,801, filed as application No. PCT/EP97/07224 on Dec. 23, 1997, now Pat. No. 6,170,717.

(30) Foreign Application Priority Data

Dec. 27, 1996 (GB) .............................. 9626960

(51) Int. Cl.$^7$ .............................................. B65D 83/54
(52) U.S. Cl. .................................. 222/402.2; 222/402.1
(58) Field of Search .......................... 222/328, 402.19, 222/402.2, 402.24, 402.1, 547, 546

(56) References Cited

U.S. PATENT DOCUMENTS

| 4,863,073 A | 9/1989 | Burt et al. |
|---|---|---|
| 4,867,352 A | 9/1989 | Meshberg |
| 4,944,433 A | 7/1990 | Knecht et al. |
| 5,037,012 A | 8/1991 | Langford |
| 5,632,421 A | 5/1997 | Colombo |
| 5,674,472 A | 10/1997 | Akehurst et al. |
| 5,697,532 A | 12/1997 | Wilde et al. |
| 5,904,274 A | 5/1999 | Warby et al. |
| 6,170,717 B1 | 1/2001 | Di Giovanni et al. |
| 6,315,173 B1 | 11/2001 | Di Giovanni et al. |
| 6,510,969 B2 * | 1/2003 | Di Giovanni et al. ... 222/402.2 |

FOREIGN PATENT DOCUMENTS

| EP | 0 326 122 A | 8/1989 | |
|---|---|---|---|
| EP | 0 774 423 A | 5/1997 | |
| GB | 2 004 526 A | 4/1979 | |
| GB | 2 206 099 | 12/1988 | |
| GB | 2 206 100 A | 12/1988 | |
| GB | 2307224 A * | 5/1997 | .......... B65D/83/14 |
| WO | 90/08075 | 7/1990 | |
| WO | 94/29192 | 12/1994 | |

* cited by examiner

Primary Examiner—Kenneth Bomberg
(74) Attorney, Agent, or Firm—J. Michael Strickland (57) ABSTRACT

Valve for an aerosol container for dispensing a suspension of a substance in a liquid propellant contained therein. The valve comprises a valve body (1) having at least one orifice (16) to allow a quantity of the suspension to pass from the container into the valve. The valve further comprises a ring (18) disposed around the valve body (1), the ring being positioned below the at least one orifice to reduce the volume of suspension that can be accommodated within the container below the at least one orifice when the container is orientated with the valve at the bottom, the ring having at least one portion of reduced axial thickness to provide a trough (19) around the valve body below the at least one orifice.

36 Claims, 5 Drawing Sheets

VALVE FOR AEROSOL CONTAINER

This application is a continuation of U.S. application Ser. No. 09/957,916, flied Sep. 21, 2001, now U.S. Pat. No. 6,510,969 which is a continuation of U.S. application Ser. No. 09/709,084, filed Nov. 10, 2000, now U.S. Pat. No. 6,315,173; which is a continuation of U.S. application Ser. No. 09/331,801, filed Sep. 13, 1999, now U.S. Pat. No. 6,170,717, for which Application PCT/EP97/07224 was flied internationally on Dec. 23, 1997; the disclosures of which are incorporated herein by reference in their entirety.

In dispensing a solid in aerosol form it is common to use what is known as a suspension aerosol. This involves the use of a liquid propellant in which a solid to be dispensed is suspended. There is inevitably some difference, however slight, between the respective specific gravities of the propellant and the solid to be dispensed, which means that, with the passage of time and in the absence of other overriding interactions, the two components tend to separate in the container, with a lighter component going to the top or a heavier component going to the bottom over time.

In some pharmaceutical aerosols the particles of medicament are more dense than the propellant and hence the particles tend to sediment out to the bottom of the container. This phenomenon may be accentuated by the additional structuring of the medicament presentation necessary to enhance its physical stability, for example by controlled flocculation thereof. Controlled flocculation of the suspension may increase the effective particle size in dispersion from less than 10 μm to greater than 100 μm. A squared dependency on particle radius will directly increase the sedimentation rate in such circumstances.

Users of suspension aerosols are always instructed before use to shake the container well. However, even a short interval between the conclusion of the shaking and the act of dispensing a charge from the aerosol is sufficient to allow some sedimentation to occur. This represents a particular problem where the suspended material is a medicament, since it can result in the patient receiving a dose which, although of the correct volume, contains either too little or too much of the medicament.

This problem has been found to be particularly acute in the development of CFC-free aerosol formulations using propellant 1,1,1,2-tetrafluoroethane, also known as HFA134a, which is less dense than conventional CFC containing propellants. With some aerosol drug formulations using this propellant, when the container is orientated with the valve at the bottom, the drug particles rapidly sediment onto and around the valve, and with vibration caused by, for example, transportation, find their way into the valve body. The trapped drug is then not fully dispensed, even on shaking due to the confinement of the valve body, and on discharge of valve actuation the trapped drug enters the metering chamber which leads to a high drug content in the dose delivered by the following actuation. This problem is especially pronounced where the drug is fluticasone propionate.

UK Patent No. 2195986 describes an aerosol valve wherein the pick-up point, i.e. the point at which liquid passes from the interior of the container into the sampling chamber of the valve, is at a location which, when the container is orientated with the valve at the bottom, is spaced an appreciable vertical distance from the nearest substantially horizontal surface. Whilst this valve ensures that the liquid entering the metering chamber following a dispensing operation comes from above the nearest region where sedimented drug particles might gather, any sedimenting drug particles that might be drawn into the sampling chamber together with any drug particles that sediment out of the suspension within the sampling chamber tend to be trapped and are not dispensed on shaking. Furthermore, by deliberately placing the pick-up point appreciably higher than the lowest point in the container, a significant quantity of the contents of the container cannot be dispensed, which results in considerable wastage.

It is an object to provide a valve which alleviates these problems.

According to the present invention there is provided a valve for an aerosol container for dispensing a suspension of a substance in a liquid propellant contained herein, the valve comprising a valve body having at least one orifice to allow a quantity of the suspension to pass from the container into the valve, characterised in that the valve further comprises a ring disposed around the valve body, the ring being positioned below the at least one orifice to reduce the volume of suspension that can be accommodated within the container below the at least one orifice when the container is orientated with the valve at the bottom, the ring having at least one portion of reduced axial thickness to provide a trough around the valve body below the at least one orifice.

By providing a ring below the at least one orifice to reduce the volume of suspension that can be accommodated within the container below the orifice(s) when the container is orientated with the valve at the bottom, it ensures that most of the contents of the container may be dispensed to reduce wastage, while the trough around the valve body below the orifice(s) provided by the at least one portion of reduced axial thickness serves to accommodate any drug particle sediment so ensuring that the suspension entering the sampling chamber comes from above the region where any sedimented drug particles might gather.

Preferably, the valve is a metering valve comprising a metering chamber, a sampling chamber, a transfer passage through which a quantity of suspension can pass from the sampling chamber to the metering chamber, and a valve stem having a dispensing passage through which a dose of suspension can be dispensed from the metering chamber, the valve stem being slideably moveable within the valve body such that in a first position the dispensing passage is isolated from the metering chamber and the metering chamber is in communication with the sampling chamber via the transfer passage, and in a second position the dispensing passage is in communication with the metering chamber and the transfer passage is isolated from the metering chamber the valve body having a plurality of orifices to allow a quantity of the suspension to pass from the container into the sampling chamber.

By providing a valve body having a plurality of orifices to allow the suspension to pass from the container into the sampling chamber, the suspension may flow freely through the sampling chamber so allowing the suspension contained within the sampling chamber and the container to mix when the container is shaken and so disperse any drug particle sediment within the sampling chamber.

Suitably the orifices are slots extending in a substantially axial direction. Preferably the slots extend substantially the entire axial length of the sampling chamber.

By providing slots the length of the sampling chamber the suspension may flow freely through the entire sampling chamber, so allowing maximum dispersion of drug particle sediment within the sampling chamber.

Preferably there are more than two slots.

Suitably the ring further comprises a seat to locate a gasket between the container and valve for sealing the container.

By providing a seat on the ring to locate the gasket, the gasket is reduced in size, and the area of gasket exposed to the contents of the container is also reduced.

Suitably the ring further comprises a plurality of vanes separated by slots at its periphery and extending substantially upwardly when the container is orientated with the valve at the bottom.

By providing vanes separated by slots at the periphery of the ring the suspension is made to flow around the vanes and through the slots when the container is shaken, and the resulting swirling motion of the suspension helps to disperse any drug particle sediment on and around the ring.

Suitably the substance to be dispersed is a medicament suspended in liquefied HFA134a. Preferably the medicament is fluticasone propionate.

The invention will now be described further with reference to the accompanying drawings in which.

Figure 1:
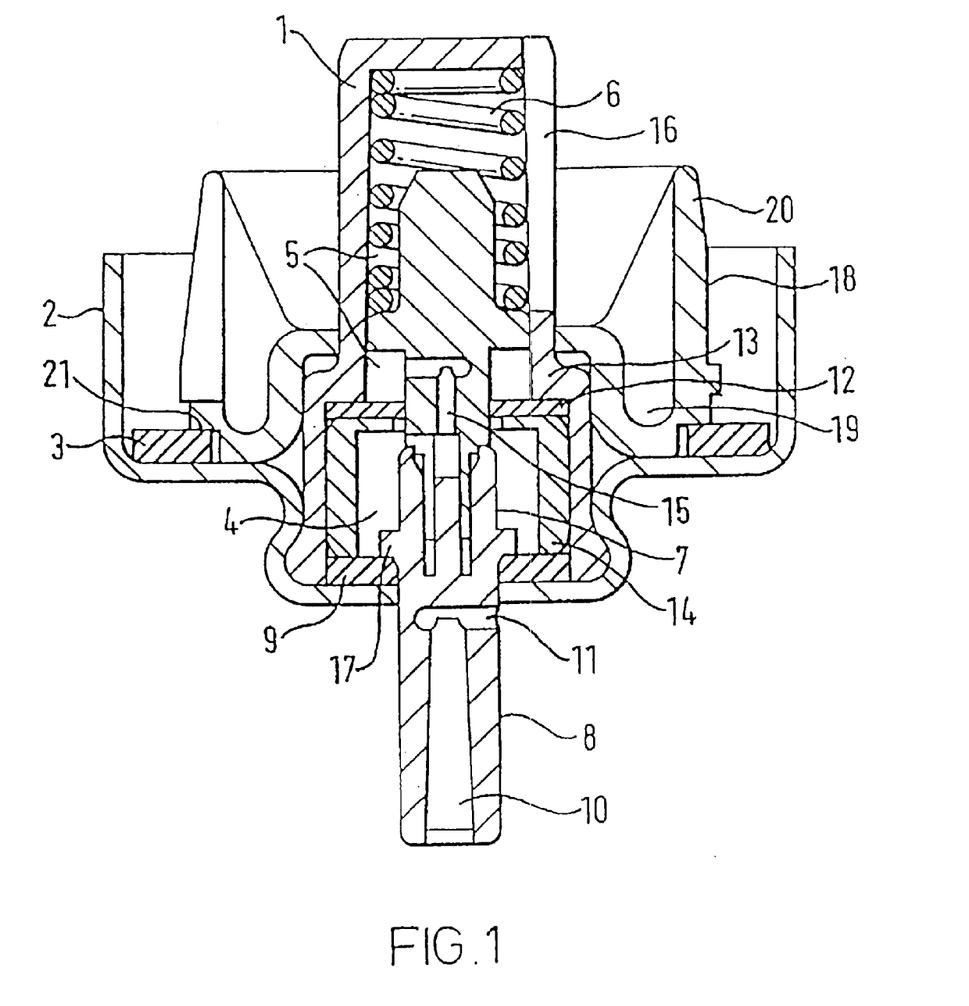
FIG. 1 is a section through a metering valve according to a first embodiment of the invention.

The valve according to a first embodiment of the invention as shown in FIG. 1 comprises a valve body 1 sealed in a ferrule 2 by means of crimping, the ferrule itself being set on the neck of a container (not shown) with the interposition of a gasket 3 in a well-known manner. The container is filled with a suspension of a medicament in liquid propellant HFA134a. Medicaments suitable for this purpose are, for example for the treatment of respiratory disorders such as asthma, bronchitis, chronic obstructive pulmonary diseases and chest infections. Additional medicaments may be selected from any other suitable drug useful in inhalation therapy and which may be presented as a suspension. Appropriate medicaments may thus be selected from, for example, analgesics, e.g. codeine, dihydromorphine, ergotamine, fentanyl or morphine; anginal preparations, e.g. diltiazem; antiallergics, e.g. cromoglycate, ketotifen or neodocromil; antiinfectives e.g. cephalosporins, penicillins, streptomycin, sulphonamides, tetracyclines and pentamidine; antihistamines, e.g. methapyrilene; anti-inflammatories e.g. fluticasone propionate, beclomethasone dipropionate, flunisolide, budesonide, or triamcinolone acetonide; antitussives, e.g. noscapine; bronchodilators, e.g. salmeterol, salbutamol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol orciprenaline, or (–)-4-amino-3,5-dichloro-α-[[[6-[2-(2-pyridinyl)ethoxy]-hexyl]amino]methyl] benzenemethanol; diuretics, e.g. amiloride; anticholinergics e.g. ipratropium, atropine or oxitropium; hormones, e,g, cortisone, hydrocortisone or prednisolone; xanthines e.g. aminophylline, choline theophyllinate, lysine theophyllinate or theophylline and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimise the activity and/or stability of the medicament. Preferred medicaments are salbutamol, salbutamol sulphate, salmeterol, salmeterol xinafoate, fluticasone propionate, beclomethasone dipropionate and terbutaline sulphate. It is to be understood that the suspension of medicament may consist purely of one or more active ingredients.

The valve body 1 is formed at its lower part with a metering chamber 4, and its upper part with a sampling chamber 5 which also acts as a housing for a return spring 6. The words "upper" and "lower" are used for the container when it is in a use orientation with the neck of the container and valve at the lower end of the container which corresponds to the orientation of the valve as shown in FIG. 1. Inside the valve body 1 is disposed a valve stem 7, a part 8 of which extends outside the valve through lower stem seal 9 and ferrule 2. The stem part 8 is formed within an inner axial or longitudinal canal 10 opening at the outer end of the stem and in communication with a radial passage 11.

The upper portion of stem 7 has a diameter such that it can pass slideably through an opening in an upper stem seal 12 and will engage the periphery of that opening sufficiently to provide a seal. Upper stem seal 12 is held in position against a step 13 formed in the valve body 1 between the lower and upper parts by a sleeve 14 which defines the metering chamber 4 between lower stem seal 9 and upper stem seal 12. The valve stem 7 has a passage 15 which, when the stem is in the inoperative positive shown, provides a communication between the metering chamber 4 and sampling chamber 5, which itself communicates with the interior of the container via orifices 16 formed in the side of the valve body 1. The orifices 16 comprise three slots arranged equi-angularly around the valve body 1 and extending in an axial direction with respect thereto, each slot having a width of approximately 1 mm and a length slightly less than the length of the sampling chamber 5 so that the suspension within the container can flow freely through the entire sampling chamber 5.

Valve stem 7 is biased downwardly to the inoperative position by return spring 6 and is provided with a shoulder 17 which abuts against lower stem seal 9. In the inoperative position as shown in FIG. 1 shoulder 17 abuts against lower stem seal 9 and radial passage 11 opens below lower stem seal 9 so that the metering chamber 4 is isolated from canal 10 and suspension inside cannot escape.

Figure 3:
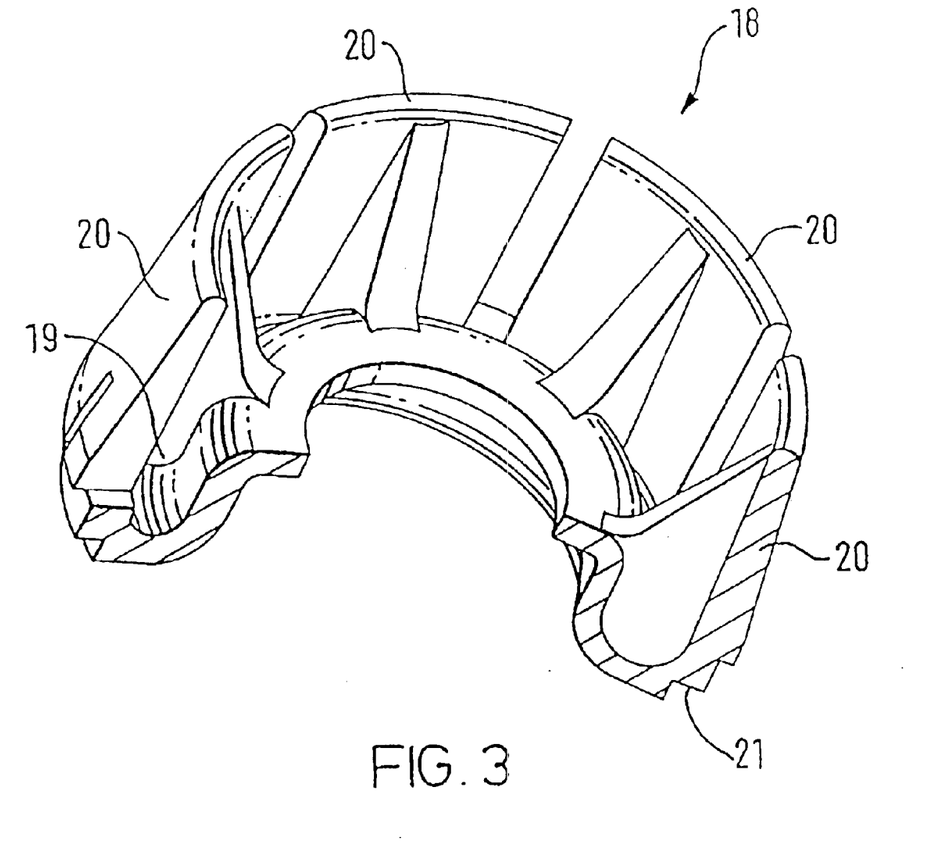
FIG. 3 is a partly cut away perspective view of a ring for use with a valve according to the invention.
Figure 4:
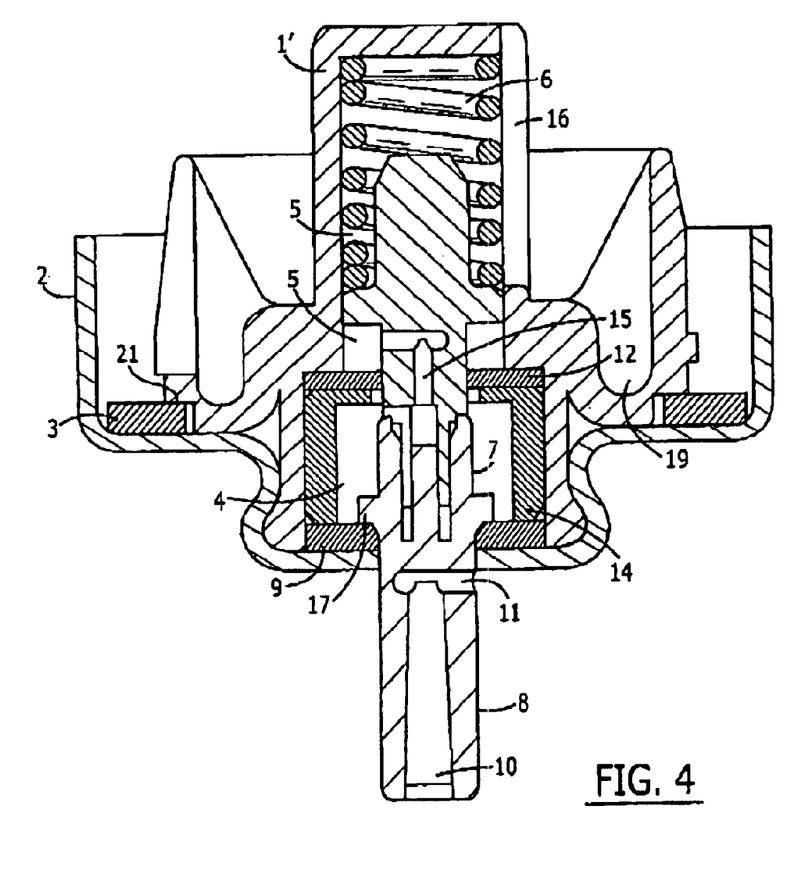
FIG. 4 is a section through a metering valve having a valve body and a ring integrally formed according to a third embodiment of the invention.
Figure 5:
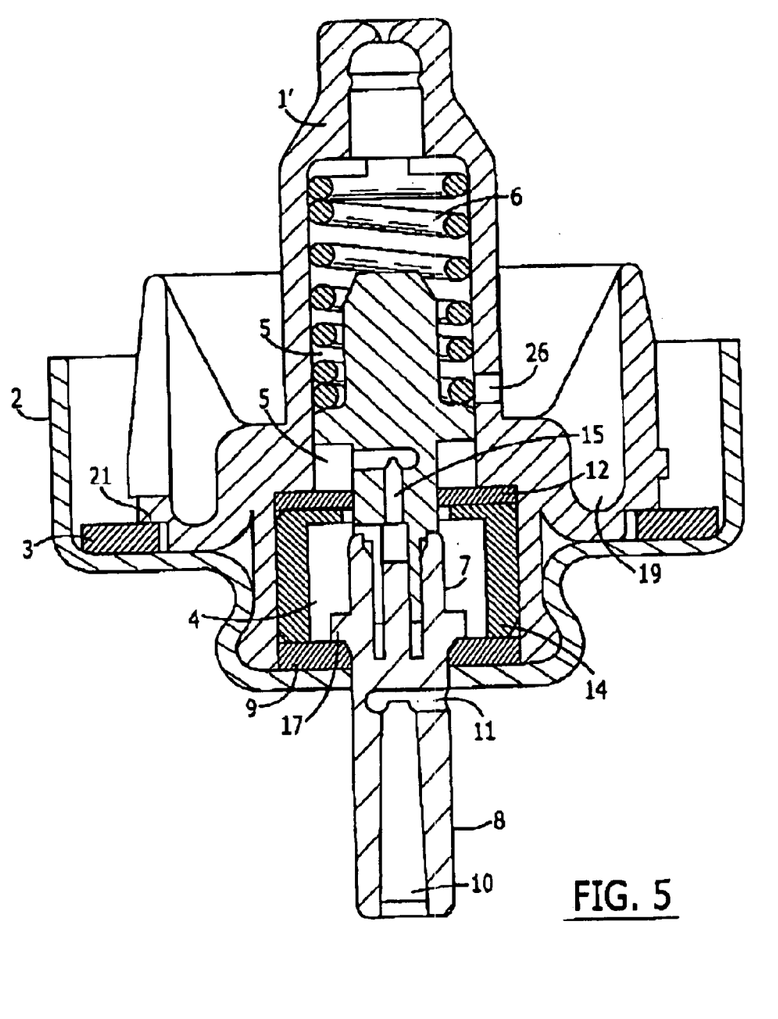
FIG. 5 is a section through a metering valve having a valve body and a ring integrally formed according to a fourth embodiment of the invention.

A ring 18 is disposed around the valve body below the slots, and is formed with a number of portions of reduced axial thickness giving a "U" shaped cross section extending in a radial direction so as to form a number of troughs 19 around the valve body. As seen in FIGS. 1 and 3, the ring is formed as a separate component made of nylon or any other suitable material, and has an inner annular contacting rim of a diameter mutable to provide a friction fit over the upper part of valve body 1, the ring seating against step 13 below the slots 16. However, the ring 18 maybe alternatively formed as an integrally molded part of valve body 1, as illustrated in by integrally formed valve body and ring 1' FIGS. 4 and 5.

The outer wall of the ring is extended in an axial direction and is formed with a number of equi-angularly spaced slots to create vanes 20 which extend upwards from the lower part of the ring, as best seen in FIG. 3. In the ring depicted in FIG. 3, there are six slots and six vanes, though not all are shown in view of the cut away portion. However, it will be clear that more or fewer slots and vanes could be used. The lower part of the ring is further provided with a seat 21 for gasket 3 which helps to locate the gasket in the correct position during assembly and also allows the inner diameter of the gasket to be increased, thereby reducing the mass of the gasket and the area of gasket exposed to the material within the container. This can offer a significant advantage where there are problems with impurities being leached out of the gasket into the material contained.

To use the device, the container is shaken to homogenise the suspension within the container. As the container is shaken, the suspension in the container flows freely through the slots 16 in the sampling chamber 5, so ensuring that the suspension in the sampling chamber is thoroughly mixed with the suspension in the container. Not only does this ensure homogeneity of suspension within the container and sampling chamber, but the flow of suspension also serves to disperse any drug particle sediment that may have precipitated out of suspension within the sampling chamber 5. Shaking of the container also causes the suspension to flow around the vanes 20 and the resulting turbulence and swirling motion of the suspension helps to disperse any drug particle sediment on and around the ring.

The user then depresses the valve stem 7 against the force of the spring 6. When the valve stem is depressed, both ends of the passage 15 come to lie on the side of upper stem seal 12 remote from the metering chamber 4. Thus a dose is metered within the metering chamber. Continued depression of the valve stem will move the radial passage 11 into the metering chamber 4 while the upper stem seal 12 seals against the valve stem body. Thus, the metered dose can exit through the radial passage 11 and the outlet canal 10.

Releasing the valve stem causes it to return to the illustrated position under the force of the spring 6. The passage 15 then once again provides communication between the metering chamber 4 and the sampling chamber 5. Accordingly, at this stage liquid passes under pressure from the container through slots 16, through the passage 15 and thence into the metering chamber 4 to fill it.

It can be seen that in the operative orientation of the container and valve as shown, the "U" shaped configuration of the ring 18 around the valve body provides a trough 19 which lies an appreciable distance below the slots 16. The trough serves to accommodate any drug particle sediment that fails to be re-dispersed into suspension, and thus ensures that the suspension entering the sampling chamber 5 through the slots 16 is drawn from a region containing homogenous suspension which is free of drug particle sediment.

The ring 18 further serves to reduce the volume of suspension that can be accommodated within the container below the slots 16. This ensures that most of the contents of the container may be dispensed, the only quantity of suspension that need be wasted corresponding to the reduced volume remaining below the slots after the suspension level has fallen below the level from which it may enter the sampling chamber.

Tables 1 and 2 present end of life actuation weights in mg delivered from two sets of five inhalers each. Both tables show data derived from inhalers containing the equivalent of 160 actuations of a suspension of fluticasone propionate in liquefied HFA134a with a target delivery of 120 actuations plus a 40 actuation overfill to allow for ullage and leakage. Only data from actuation number 115 is shown as the data for both sets of inhalers is consistent up to this point. Table 1 shows data from the first set of five conventional inhalers having valves without a ring. Table 2 shows data from the second set of five inhalers having valves with a ring according to the invention:

TABLE 1

End of Life Actuation weights for valve without ring

| Actuation No. | Actuation weights (mg) | | | | |
|---|---|---|---|---|---|
| | Inhaler 1 | Inhaler 2 | Inhaler 3 | Inhaler 4 | Inhaler 5 |
| 115 | 61 | 60 | 62 | 62 | 61 |
| 116 | 62 | 62 | 62 | 61 | 61 |
| 117 | 61 | 60 | 62 | 61 | 60 |
| 118 | 61 | 61 | 62 | 60 | 60 |
| 119 | 42 | 60 | 62 | 45 | 31 |
| 120 | 61 | 61 | 62 | 61 | 62 |
| 121 | 60 | 59 | 61 | 62 | 60 |
| 122 | 60 | 59 | 61 | 61 | 60 |
| 123 | 62 | 61 | 62 | 61 | 61 |
| 124 | 63 | 61 | 62 | 61 | 60 |
| 125 | 62 | 42 | 47 | 47 | 59 |
| 126 | 62 | 59 | 64 | 63 | 60 |
| 127 | 49 | 61 | 53 | 42 | 37 |
| 128 | 61 | 61 | 63 | 61 | 62 |
| 129 | 63 | 57 | 39 | 63 | 63 |
| 130 | 63 | 62 | 63 | 63 | 62 |
| 131 | 60 | 41 | 34 | 38 | 45 |
| 132 | 62 | 61 | 61 | 60 | 59 |
| 133 | 44 | 43 | 39 | 49 | 61 |
| 134 | 60 | 62 | 58 | 62 | 60 |
| 135 | 32 | 60 | 17 | 26 | 44 |
| 136 | 58 | 61 | 60 | 59 | 61 |
| 137 | 49 | 54 | 58 | 51 | 59 |
| 138 | 48 | 45 | 34 | 59 | 59 |
| 139 | 25 | 16 | 14 | 29 | 16 |
| 140 | 37 | 18 | 20 | 5 | 12 |
| 141 | 6 | 8 | 5 | 7 | 18 |
| 142 | 47 | 23 | 30 | 27 | 38 |
| 143 | 10 | 29 | 23 | 15 | 22 |
| 144 | 9 | 16 | 18 | 31 | 36 |
| 145 | 30 | 37 | 29 | 33 | 48 |
| 146 | 42 | 41 | 32 | 30 | 46 |

TABLE 2

End of Life Actuation weights for valve with ring

| Actuation No. | Actuation weights (mg) | | | | |
|---|---|---|---|---|---|
| | Inhaler 1 | Inhaler 2 | Inhaler 3 | Inhaler 4 | Inhaler 5 |
| 115 | 60 | 61 | 61 | 60 | 62 |
| 116 | 62 | 61 | 61 | 61 | 63 |
| 117 | 61 | 60 | 60 | 60 | 61 |
| 118 | 61 | 61 | 61 | 60 | 62 |
| 119 | 60 | 59 | 60 | 60 | 61 |
| 120 | 60 | 61 | 60 | 60 | 62 |
| 121 | 60 | 59 | 60 | 59 | 62 |
| 122 | 60 | 60 | 59 | 59 | 60 |
| 123 | 61 | 61 | 61 | 61 | 61 |
| 124 | 61 | 60 | 61 | 61 | 63 |
| 125 | 61 | 60 | 60 | 59 | 31 |
| 126 | 61 | 60 | 61 | 60 | 62 |
| 127 | 61 | 59 | 61 | 60 | 61 |
| 128 | 61 | 61 | 61 | 60 | 63 |
| 129 | 62 | 58 | 61 | 61 | 57 |
| 130 | 62 | 61 | 61 | 61 | 63 |
| 131 | 60 | 61 | 61 | 60 | 60 |
| 132 | 61 | 60 | 61 | 61 | 62 |
| 133 | 61 | 61 | 61 | 60 | 62 |
| 134 | 61 | 61 | 61 | 61 | 62 |
| 135 | 61 | 60 | 60 | 60 | 62 |
| 136 | 61 | 60 | 60 | 60 | 62 |
| 137 | 59 | 60 | 59 | 58 | 60 |
| 138 | 59 | 59 | 59 | 59 | 60 |
| 139 | 59 | 55 | 59 | 60 | 55 |
| 140 | 31 | 61 | 61 | 59 | 60 |
| 141 | 25 | 48 | 61 | 60 | 33 |
| 142 | 61 | 60 | 61 | 60 | 60 |
| 143 | 21 | 9 | 23 | 20 | 26 |
| 144 | 17 | 25 | 32 | 26 | 25 |
| 145 | 44 | 32 | 36 | 25 | 35 |

TABLE 2-continued

End of Life Actuation weights for valve with ring

| Actuation | Actuation weights (mg) | | | | |
|---|---|---|---|---|---|
| No. | Inhaler 1 | Inhaler 2 | Inhaler 3 | Inhaler 4 | Inhaler 5 |
| 146 | 17 | 9 | 26 | 19 | 28 |

From Table 1 it can be seen that actuation weight starts to become fairly inconsistent after actuation number 124 for valves without the ring, whereas from Table 2 it can be seen that actuation weight remains fairly consistent up to actuation number 137 and thereafter rapidly tails off for those valves according to the invention incorporating the ring. It is therefore clear that the ring has a significant effect on end of life actuation weight delivered.

Figure 2:
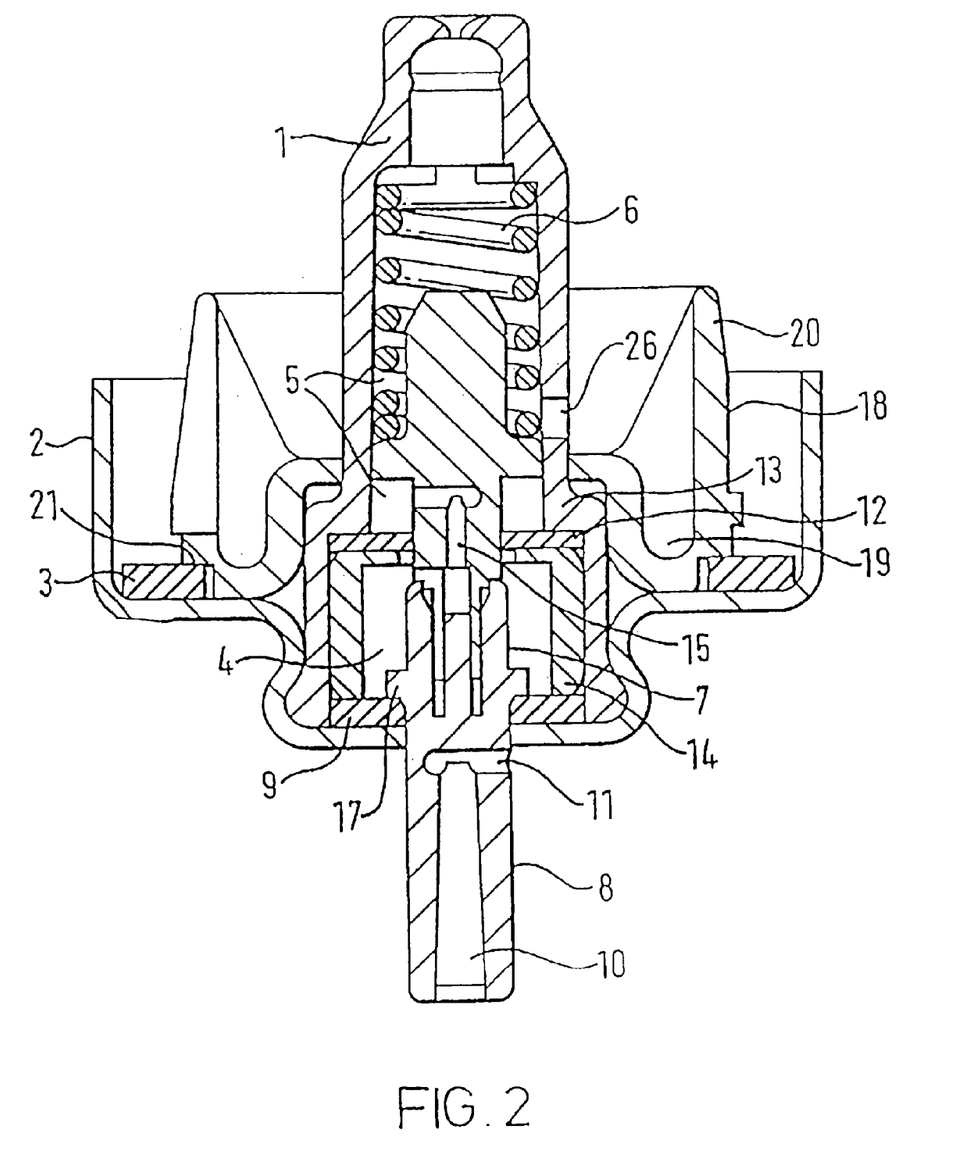
FIG. 2 is a section through a metering valve according to a second embodiment of the invention.

A valve according to a second embodiment of the invention as shown in FIG. 2 is a variant of the valve shown in FIG. 1 in which corresponding elements have been given the same reference numerals as are used in FIG. 1. The main difference between the two embodiments is that the valve of FIG. 2 uses a different design of valve body 1 which has a single orifice 26 allowing communication between sampling chamber 5 and the interior of the container. The valve is operated in exactly the same manner as described with respect to the valve shown in FIG. 1. The valve shown in FIG. 2 might be used with suspensions wherein the problem of sedimentation within the sampling chamber is not so acute but wherein sedimentation around the valve nonetheless remains a problem.

Table 3 demonstrates the improved dose reproducibility achieved using a valve according to the first embodiment of the invention with a body having three slots as shown in FIG. 1 compared to a valve according to the second embodiment of the invention with a body having a single orifice as shown in FIG. 2 when used to dispense a suspension of fluticasone propionate in liquefied HFA134a. The figures given in the table are average dose weights dispensed from at least five inhalers. For each inhaler, doses from two actuations were measured prior to subjecting each inhaler to a vibration test to simulate the effects of transportation, after which doses from two further actuations were measured:

TABLE 3

Effect of vibration on dose delivered

| Valve type | Dose ($\mu$g) prior to vibration | | Dose ($\mu$g) after vibration | |
|---|---|---|---|---|
| | 1st actuation | 2nd actuation | 1st actuation | 2nd actuation |
| Body with single orifice | 233 | 246 | 217 | 688 |
| Body with three slots | 288 | 285 | 275 | 317 |

The data presented in Table 3 clearly shows that the characteristics of extreme dose variability experienced with valves having a single sampling point (orifice), which is due to the highly sedimentary nature of fluticasone propionate in liquefied HFA134a, are considerably reduced with the three slot body.

It will be understood that the present disclosure is for the purpose of illustration only and the invention extends to modifications, variations and improvements thereto.

We claim:

1. A metering valve for use in an aerosol container for dispensing an aerosol suspension having a longitudinal axis which, in a use orientation of the valve, extends in an upward-downward direction, said metering valve comprising:
   a hollow, longitudinally extending valve body having an inner volume, said valve body having at least one orifice to allow a quantity of the suspension from the container to pass into said inner volume;
   a ring extending laterally outwardly from said valve body from a position disposed below said orifice, said ring providing a trough about said vale body that extends longitudinally in the downward direction and is arranged below said orifice;
   a metering chamber disposed in said inner volume of said valve body;
   a sampling chamber disposed in said inner volume of said valve body, the entire volume of said sampling chamber being positioned above said metering chamber with said orifice in said valve body opening thereto such that the suspension passes into said sampling chamber;
   a valve stem mounted far axial sliding movement in said valve body between a first position and a second position, said valve stem having a transfer passage for transferring the suspension from said sampling chamber into said metering chamber and a dispensing passage disposed below said transfer passage for dispensing the suspension from said metering chamber,
   wherein in said first position said transfer passage places said sampling and metering chambers in fluid communication such that said metering chamber is able to be filled with a metered dose of the suspension from said sampling chamber and said dispensing passage is isolated from said metering chamber, and
   wherein in said second position said transfer passage is isolated from said metering chamber while said dispensing passage is placed in fluid communication with said metering chamber to dispense the metered dose of the suspension from said metering chamber.

2. The metering valve of claim 1, wherein said trough has a U-shaped longitudinal cross-section.

3. The metering valve of claim 1, wherein said ring and said valve body are integrally formed.

4. The metering valve of claim 1, wherein said orifice opens into said sampling chamber when said valve stem is in said second position.

5. The metering valve of claim 1, wherein said inner volume of said valve body is divided into an upper section and a lower section by a seal that extends laterally across said inner volume, said seal including an aperture, said metering chamber being disposed in said lower section and said sampling chamber being disposed in said upper section.

6. The metering valve of claim 5, wherein said valve stem is sealingly slidable through said aperture in said seal.

7. The metering valve of claim 5, wherein said seal forms a common boundary between said metering and sampling chambers.

8. The metering valve of claim 1, wherein said ring has an annular wall interrupted with a plurality of slots forming a plurality of vanes, wherein, upon shaking of the aerosol container, the suspension flows around said plurality of vanes to assist in dispersion of the suspension.

9. The metering valve of claim 1, wherein said orifice comprises at least one slot extending substantially axially.

10. The metering valve or claim 9, wherein said slot extends substantially the axial length of said sampling chamber.

11. The metering valve of claim 9, wherein said metering valve includes more than two slots.

12. The metering valve of claim 1, wherein said ring further includes a seat adapted to accommodate a gasket to seal the container.

13. The metering valve of claim 11, wherein said ring has an annular wall interrupted with a plurality of slots forming at least three vanes, wherein, upon shaking of the aerosol container, the suspension flows around said vanes to assist in dispersion of the suspension.

14. The metering valve of claim 1, wherein said trough includes a plurality of angularly spaced apart trough segments.

15. The metering valve of claim 14, wherein said ring includes an annular, longitudinally-arranged wall with an inner surface that faces said trough and from which project longitudinally-arranged rib portions that divide said trough into said trough segments.

16. The metering valve of claim 15, wherein said annular wall is interrupted by a plurality of angularly spaced-apart longitudinal slots, each of said slots being positioned between an adjacent pair of said ribs.

17. The metering valve of claim 1, wherein the suspension includes a medicament selected from the group consisting of analgesics, anginal preparations, antiallergics, antiinfectives, antihistamines, antiinflammatories, antitussives, diuretics, anticholinergics, hormones, xanthines, therapeutic proteins, therapeutic peptides, and combinations thereof in liquefied HFA 134a.

18. The metering valve of claim 17, wherein said medicament comprises fluticasone propionate.

19. A metering valve for use in an aerosol container for dispensing an aerosol suspension having a longitudinal axis which, in a use orientation of the valve, extends in an upward-downward direction, said metering valve comprising:

a hollow, longitudinally extending valve body having an inner volume, said valve body having at least one orifice to allow a quantity of the suspension from the container to pass into said inner volume, said orifice having a lowermost edge;

a ring extending laterally outwardly from said valve body from a position axially spaced from said lowermost edge of said orifice in the downward direction, said ring providing a trough about said vale body that is axially spaced from said lowermost edge of said orifice in the downward direction;

a metering chamber disposed in said inner volume of said valve body;

a sampling chamber disposed in said inner volume of said valve body, the entire volume of said sampling chamber being positioned above said metering chamber with said orifice in said valve body opening thereto such that the suspension passes into said sampling chamber;

a valve stem mounted for axial sliding movement in said valve body between a first position and a second position, said valve stem having a transfer passage for transferring the suspension from said sampling chamber into said metering chamber and a dispensing passage disposed below said transfer passage for dispensing the suspension from said metering chamber, wherein in said first position said transfer passage places said sampling and metering chambers in fluid communication such that said metering chamber is able to be filled with a metered dose of the suspension from said sampling chamber and said dispensing passage is isolated from said metering chamber, and wherein in said second position said transfer passage is isolated from said metering chamber while said dispensing passage is placed in fluid communication with said metering chamber to dispense the metered dose of the suspension from said metering chamber.

20. The metering valve of claim 19, wherein said trough has a U-shaped longitudinal cross-section.

21. The metering valve of claim 19, wherein said ring and said valve body are integrally formed.

22. The metering valve of claim 19, wherein said orifice opens into said sampling chamber when said valve stem is in said second position.

23. The metering valve of claim 19, wherein said inner volume of said valve body is divided into an upper section and a lower section by a seal that extends laterally across said inner volume, said seal including an aperture, said metering chamber being disposed in said lower section and said sampling chamber being disposed in said upper section.

24. The metering valve of claim 23, wherein said valve stem is sealingly slidable through said aperture in said seal.

25. The metering valve of claim 23, wherein said seal forms a common boundary between said metering and sampling chambers.

26. The metering valve of claim 19, wherein said ring has an annular wall interrupted with a plurality of slots forming a plurality of vanes, wherein, upon shaking of the aerosol container, the suspension flows around said plurality of vanes to assist in dispersion of the suspension.

27. The metering valve of claim 19, wherein said orifice comprises at least one slot extending substantially axially.

28. The metering valve of claim 27, wherein said slot extends substantially the axial length of said sampling chamber.

29. The metering valve of claim 27, wherein said metering valve includes more than two slots.

30. The metering valve of claim 19, wherein said ring further includes a seat adapted to accommodate a gasket to seal the container.

31. The metering valve of claim 29, wherein said ring has an annular wall interrupted with a plurality of slots forming at least three vanes, wherein, upon shaking of the aerosol container, the suspension flows around said vanes to assist in dispersion of the suspension.

32. The metering valve of claim 19, wherein said trough includes a plurality of angularly spaced apart trough segments.

33. The metering valve of claim 32, wherein said ring includes an annular, longitudinally-arranged wall with an inner surface that faces said trough and from which project longitudinally-arranged rib portions that divide said trough into said trough segments.

34. The metering valve of claim 33, wherein said annular wall is interrupted by a plurality of angularly spaced-apart longitudinal slots, each of said slots being positioned between an adjacent pair of said ribs.

35. The metering valve of claim 19, wherein the suspension includes a medicament selected from the group consisting of analgesics, anginal preparations, antiallergics, antiinfectives, antihistamines, antiinflammatories, antitussives, diuretics, anticholinergics, hormones, xanthines, therapeutic proteins, therapeutic peptides, and combinations thereof in liquefied HFA 134a.

36. The metering valve of claim 35, wherein said medicament comprises fluticasone propionate.

* * * * *

UNITED STATES PATENT AND TRADEMARK OFFICE
CERTIFICATE OF CORRECTION

PATENT NO. : 6,966,467 B2
DATED : November 22, 2005
INVENTOR(S) : Patrick Di Giovanni et al.

It is certified that error appears in the above-identified patent and that said Letters Patent is hereby corrected as shown below:

<u>Title page,</u>
Item [56], References Cited, U.S. PATENT DOCUMENTS, insert:
-- 3,176,890    04/06/65    POTAPENKO, et al.
   3,841,602    10/15/74    MILDERN
   4,349,135    09/14/82    BUSSELET
   5,126,123    06/30/92    JOHNSON
   5,190,190    03/02/93    FUDALLA
   5,385,140    01/31/95    SMITH
   5,630,530    05/20/97    GEIER, et al.
   6,112,950    09/05/00    DI GIOVANNI, et al.
   6,596,260    07/22/03    BRUGGER, et al. --.
FOREIGN PATENT DOCUMENTS, insert:
-- 0125865    11/21/84    EP
   2209514    05/17/89    GB
   2303685    12/12/91    CA
   0567348    10/27/93    EP
   0583024    02/16/94    EP
   94/08651   04/28/94    PCT
   0616953    09/28/94    EP
   94/25373   11/10/94    PCT
   95/02651   01/26/95    PCT
   95/03984   02/09/95    PCT
   95/03985   02/09/95    PCT
   95/06606   03/09/95    PCT
   0642992    03/15/95    EP
   2281704    03/15/95    GB
   95/11841   05/04/95    PCT
   95/12533   05/11/95    PCT
   95/27525   10/19/95    PCT
   95/30607   11/16/95    PCT
   0692434    01/17/96    EP
   0694484    01/31/96    EP
   0696545    02/14/96    EP
   96/19198   06/27/96    PCT
   0721803    07/17/96    EP
   96/22163   07/25/96    PCT
   2298187    08/28/96    GB
   96/28367   09/19/96    PCT
   97/16360   03/09/97    PCT
   0803449    10/29/97    EP --.

UNITED STATES PATENT AND TRADEMARK OFFICE
CERTIFICATE OF CORRECTION

PATENT NO. : 6,966,467 B2
DATED : November 22, 2005
INVENTOR(S) : Patrick Di Giovanni et al.

It is certified that error appears in the above-identified patent and that said Letters Patent is hereby corrected as shown below:

Column 9,
Lines 21-29, cancel claims 17-18.

Column 10,
Lines 56-64, cancel claims 35-36.

Signed and Sealed this

Fourteenth Day of March, 2006

JON W. DUDAS
*Director of the United States Patent and Trademark Office*